(12) United States Patent
Brown et al.

(10) Patent No.: US 10,220,108 B2
(45) Date of Patent: Mar. 5, 2019

(54) DECONTAMINATION SYSTEM FOR ON-BOARD A VEHICLE

(71) Applicant: AEROCLAVE, LLC, Winter Park, FL (US)

(72) Inventors: Ronald D. Brown, Maitland, FL (US); David J. Robinson, Orlando, FL (US); Michael G. Quinoy, Maitland, FL (US); James S. Amrhein, Oviedo, FL (US)

(73) Assignee: Aeroclave, LLC, Winter Park, FL (US)

( * ) Notice: Subject to any disclaimer, the term of this patent is extended or adjusted under 35 U.S.C. 154(b) by 541 days.

(21) Appl. No.: 14/612,617

(22) Filed: Feb. 3, 2015

(65) Prior Publication Data

US 2015/0246151 A1 Sep. 3, 2015

Related U.S. Application Data

(60) Provisional application No. 61/946,077, filed on Feb. 28, 2014.

(51) Int. Cl.
*A61L 2/22* (2006.01)
*B05B 12/02* (2006.01)
(Continued)

(52) U.S. Cl.
CPC .............. *A61L 2/22* (2013.01); *B05B 7/2489* (2013.01); *B05B 12/02* (2013.01);
(Continued)

(58) Field of Classification Search
CPC ...... A61L 2/00; A61L 2/16; A61L 2/22; B05B 7/24; B05B 7/2489; B05B 12/02;
(Continued)

(56) References Cited

U.S. PATENT DOCUMENTS 5,031,834 A * 7/1991 Simpson ............. A01M 7/0082
169/15
6,343,425 B1 2/2002 Sias et al.
(Continued)

FOREIGN PATENT DOCUMENTS

EP 1116664 7/2001

*Primary Examiner* — Christopher Kim
(74) *Attorney, Agent, or Firm* — Robert L. Wolter, Esq.; Beusse Wolter Sanks & Maire, PLLC (57) ABSTRACT

A decontamination system on-board a vehicle may comprise a reservoir on-board a vehicle and the reservoir contains a disinfectant solution. The system may also include a pressurized air supply on-board the vehicle; and, one or more nozzles secured on-board the vehicle and in fluid communication with the reservoir and the pressurized air supply. In addition, one or more pumps may be on-board the vehicle and the one or more pumps are in fluid communication with the reservoir and the one or more nozzles. The system may also include a programmable controller in signal communication with the one or more pumps and pressurized air supply to activate the one or more pumps and pressurized air supply to deliver the disinfectant solution and pressurized air to the one or more nozzles, wherein the solution is dispersed in atomized form in an interior space of the vehicle to be decontaminated.

20 Claims, 10 Drawing Sheets

(51) Int. Cl.
  *B05B 7/24* (2006.01)
  *B60H 1/00* (2006.01)
  *B60H 3/00* (2006.01)
  *B05B 12/12* (2006.01)

(52) U.S. Cl.
  CPC ....... *B60H 1/00414* (2013.01); *B60H 3/0085* (2013.01); *B05B 12/12* (2013.01); *B05B 12/122* (2013.01)

(58) Field of Classification Search
  CPC ... B05B 12/12; B05B 12/122; B60H 1/00414; B60H 1/00357; B60H 3/0085; B60H 3/00
  USPC ......... 239/69, 172, 331, 332; 169/53, 24, 62
  See application file for complete search history.

(56) References Cited

U.S. PATENT DOCUMENTS

| | | |
|---|---|---|
| 6,706,243 B1 | 3/2004 | Sias et al. |
| 6,969,487 B1 | 11/2005 | Sias et al. |
| 7,008,592 B2 | 3/2006 | Sias et al. |
| 7,459,133 B2 | 12/2008 | Swank |
| 7,582,257 B2 | 9/2009 | Bedard et al. |
| 7,622,074 B2 | 11/2009 | Mielnik |
| 7,780,909 B2 | 8/2010 | Sparks |
| 7,790,104 B2 | 9/2010 | Adams |
| 2002/0030117 A1* | 3/2002 | Bryan ................. A01M 7/0014 239/61 |
| 2005/0031486 A1 | 2/2005 | Mole et al. |
| 2006/0008379 A1 | 1/2006 | Mielnik et al. |
| 2011/0091358 A1 | 4/2011 | Chen |
| 2011/0165021 A1 | 7/2011 | Berentsveig et al. |

\* cited by examiner

DECONTAMINATION SYSTEM FOR ON-BOARD A VEHICLE

CROSS-REFERENCE TO RELATED APPLICATIONS

This application claims the benefit of U.S. Provisional Application No. 61/946,077 filed Feb. 28, 2014, and is incorporated herein by reference in its entirety.

BACKGROUND OF THE INVENTION

The present invention relates to decontamination systems that generate a mist, fog or spray from a liquid disinfectant solution to sanitize surfaces within a confined area. More specifically, the invention relates to such systems that are on-board a vehicle.

Vehicles such as ambulances, fire-rescue vehicles, law enforcement vehicles etc., and the interior and exterior surfaces of such vehicles, at times may be exposed to harmful viruses, bacteria, chemicals and antimicrobial compounds. Accordingly, it is necessary to sanitize and decontaminate the vehicles to minimize and or prevent the operators or occupants of the vehicles from being exposed to these harmful elements.

Systems have been developed that generate a decontaminant spray or fog applied to internal and external surfaces of a vehicle. One such system has been developed by Aero-Clave, LLC (Winter Park, Fla.) and is sold under the brand name PADS (Portable Asset Decontamination System). PADS is a chamber that is large enough for a vehicle to enter. A disinfectant solution source and compressed air are provided in fluid communication to a plurality of nozzles spaced apart in the room. PADS also includes a control system to control pumps, valves and an air compressor to deliver the disinfectant solution to the nozzles at timed intervals to inject the disinfectant solution in a spray or fog form. A vehicle is driven in the chamber and the doors and/or windows are opened and the disinfectant in spray or fog form is distributed through the nozzles and throughout the room to disinfectant interior and exterior surfaces of the vehicle.

AeroClave has also developed a portable unit that includes a container within which a reservoir containing a disinfectant solution, an air compressor, pumps and a controller are housed. The air compressor and pumps are within a housing in the container and the housing has a top cover that has portals to which nozzles can be removable attached. Alternatively, hoses with a nozzle at one end can be attached to the portals and the nozzles can be held by hand to apply disinfectant to surfaces of a vehicle or a room, or the nozzles may be placed on a stand. As with PADS, the controller can programmed to control delivery of the disinfectant solution for timed intervals to deliver a specified volume of disinfectant solution depending on the size of the surface area to be decontaminated or the volume of a room or interior of a vehicle to be decontaminated.

SUMMARY OF THE INVENTION

The invention disclosed herein may be particularly useful for sterilizing or decontaminating spaces and surfaces of vehicles that are frequently exposed to harmful viruses, bacteria, chemicals, etc. Vehicles of particular need for such a system include first response vehicles such as ambulances. Other types of vehicles that could incorporate the described decontamination system include police vehicles, buses, trains and aircraft.

Embodiments for a decontamination system on-board a vehicle may comprise a reservoir on-board a vehicle and the reservoir contains a disinfectant solution. The system may also include a pressurized air supply on-board the vehicle; and, one or more nozzles secured on-board the vehicle and in fluid communication with the reservoir and the pressurized air supply. In addition, one or more pumps may be on-board the vehicle and the one or more pumps are in fluid communication with the reservoir and the one or more nozzles. The system may also include a programmable controller in signal communication with the one or more pumps and pressurized air supply to activate the one or more pumps and pressurized air supply to deliver the disinfectant solution and pressurized air to the one or more nozzles, wherein the solution is dispersed in atomized form in an interior space of the vehicle to be decontaminated.

The system may also include a motion detector for detecting presence of personnel in the interior space, and the motion detector is in signal communication with the programmable controller. The controller may be programmed such that when a decontamination operation is initiated the controller activates the one or more pumps and pressurized air supplied after a predetermined time during which the motion detector does not detect movement within the interior space. In addition, the system may a sensor secured on board the vehicle and in fluid flow communication with the interior space to be decontaminated and that detects levels of an active disinfectant compound of the atomized disinfectant solution. The sensor may be in signal communication with the programmable controller, which may generate signals responsive to the levels of disinfectant in the interior space.

BRIEF DESCRIPTION OF THE DRAWINGS

Embodiments are illustrated by way of example, and not by way of limitation, in the figures of the accompanying drawings and in which like reference numerals refer to similar elements and in which.

DETAILED DESCRIPTION OF THE INVENTION

A more particular description of the invention briefly described above will be rendered by reference to specific embodiments thereof that are illustrated in the appended drawings. Understanding that these drawings depict only typical embodiments of the invention and are not therefore to be considered to be limiting of its scope, the invention will be described and explained.

Figure 1:
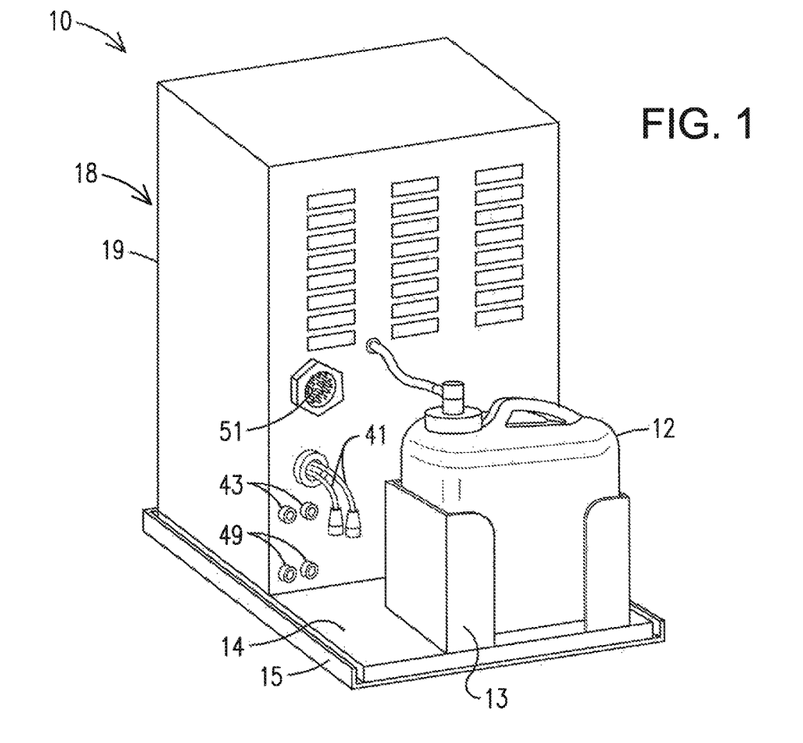
FIG. 1 is a perspective view of an on-board vehicle decontamination system in accordance with aspects of embodiments of the invention.
Figure 2:
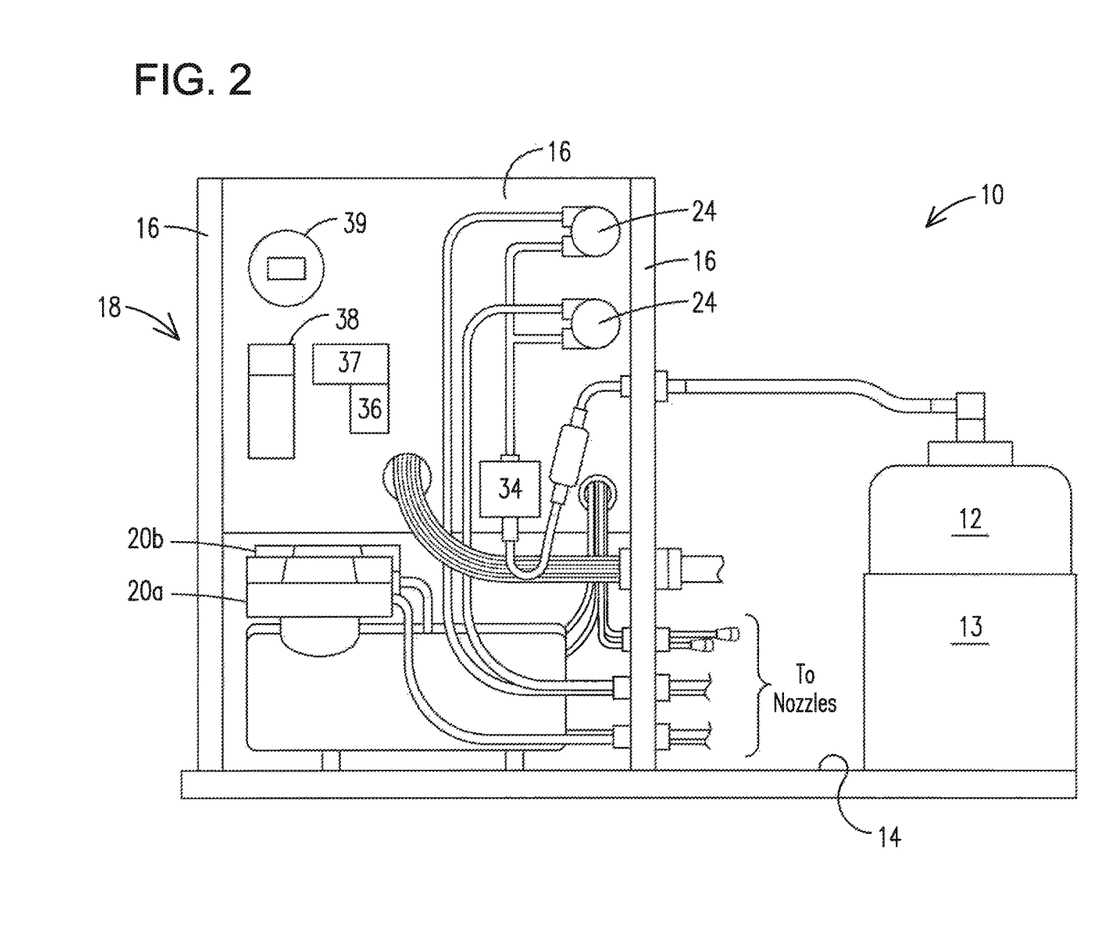
FIG. 2 is a first side elevational view of the decontamination system with the cover removed and schematically showing components of the system.
Figure 3:
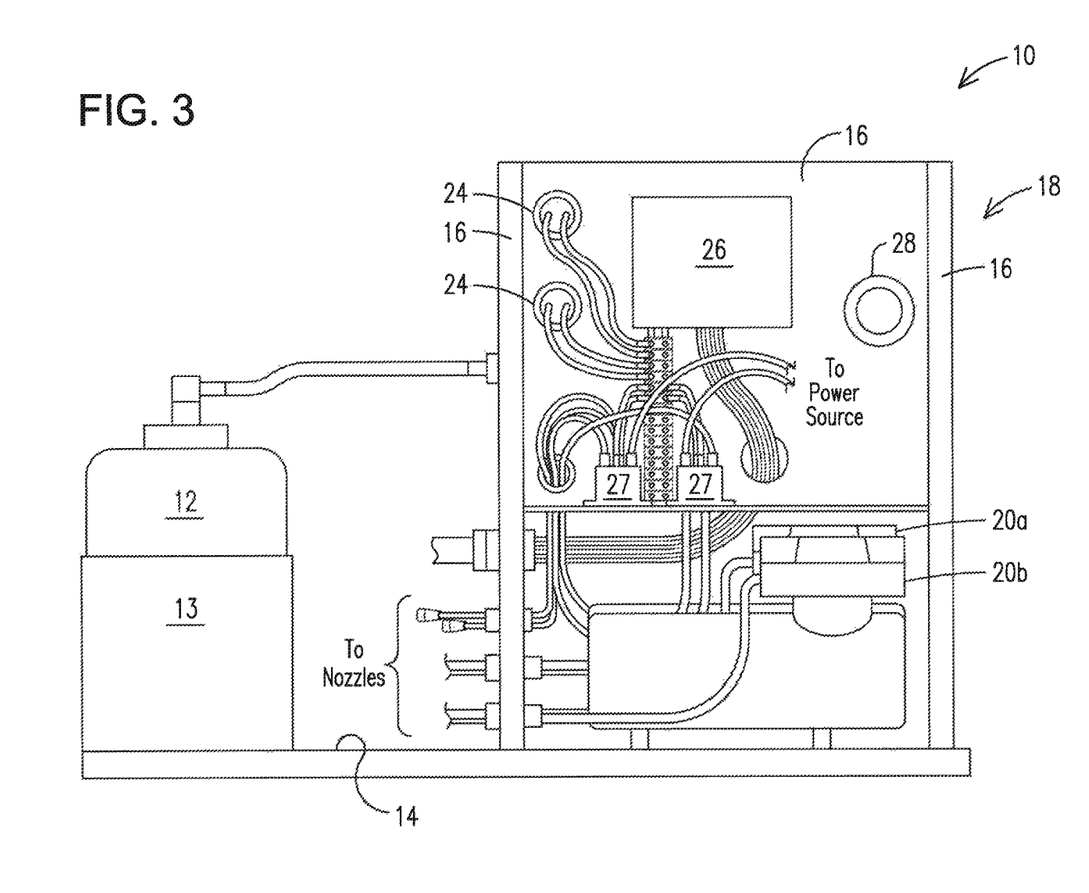
FIG. 3 is a second side elevational view of the decontamination system with the cover removed and schematically showing components of the system.

With respect to FIGS. 1-3, an embodiment of a decontamination system 10 is shown for use on-board a vehicle to decontaminate an interior space of the vehicle. As shown, the system 10 includes a reservoir 12 in which a disinfectant solution is stored. The solution is preferably an aqueous disinfectant solution. Disinfectants that may be used to disinfect surfaces of an interior space may comprise hydrogen peroxide, chlorine based compounds such as chlorine dioxide and/or hypochlorite, quarternary ammonium compounds, glutaraldehyde, formaldehyde, etc. By way of example, the disinfectant solution may include an aqueous hydrogen peroxide solution that contains about 5% by volume to about 20% by volume of hydrogen peroxide. More preferably, the solution contains about 8% by volume of hydrogen peroxide. In another embodiment, the disinfectant solution is an aqueous chlorine dioxide solution. For example, the disinfectant solution may be 0.2% by weight aqueous chlorine dioxide solution. More specifically, the solution may comprise 0.2 wt % oxychlorine compounds, 0.125 wt % n-alkyl dimethyl benzyl ammonium chloride, 0.125 wt % n-alkyl ethylbenzyl ammonium chloride, and the remaining 99.55 wt % being inert ingredients.

As further shown in FIGS. 2 and 3, the reservoir 12 and other components of the system 10 are supported on a support structure 18 that may comprise a plurality of frame members 16 fixed to a base plate 14. A removable cover 19 is positioned over the frame members 16 forming a housing within which at least some of the components of the system 10 are housed. The reservoir 12 may be disposed on a base plate 14 outside the housing. In addition, retainer walls 13 are fixed to the base plate 14 for receiving and holding the reservoir The frame members 16 may include vertically and horizontally disposed members or surfaces. Accordingly, when a component is referred to herein as being secured, mounted or affixed to the support structure 18, the component may be secured to a horizontal or vertical surface.

Again in reference to FIG. 1, electrical connectors 41 and fluid line connectors 43, 49 are affixed to cover 19. The electrical connectors 41 are provided to connect electrical lines from a power source and/or the below described controller 26 or relays 27 to components (e.g. the he below described warning lights 45 and/or motion detectors 40) are external to and remotely positioned in the vehicle relative to the support structure 18. To that end, fluid lines are connected to the connectors 43 for delivery the disinfectant solution and/or compressed air to one or more nozzles disposed at an interior and/or exterior of the vehicle. Fluid lines are connected to connectors 49 to deliver compressed air to one or more nozzles to atomize the disinfectant solution at the nozzles. In addition, for embodiments in which the below-described controller 26 is connected to a vehicle communication system, bus connector 51 is provided on the support structure 18.

Figure 4A:
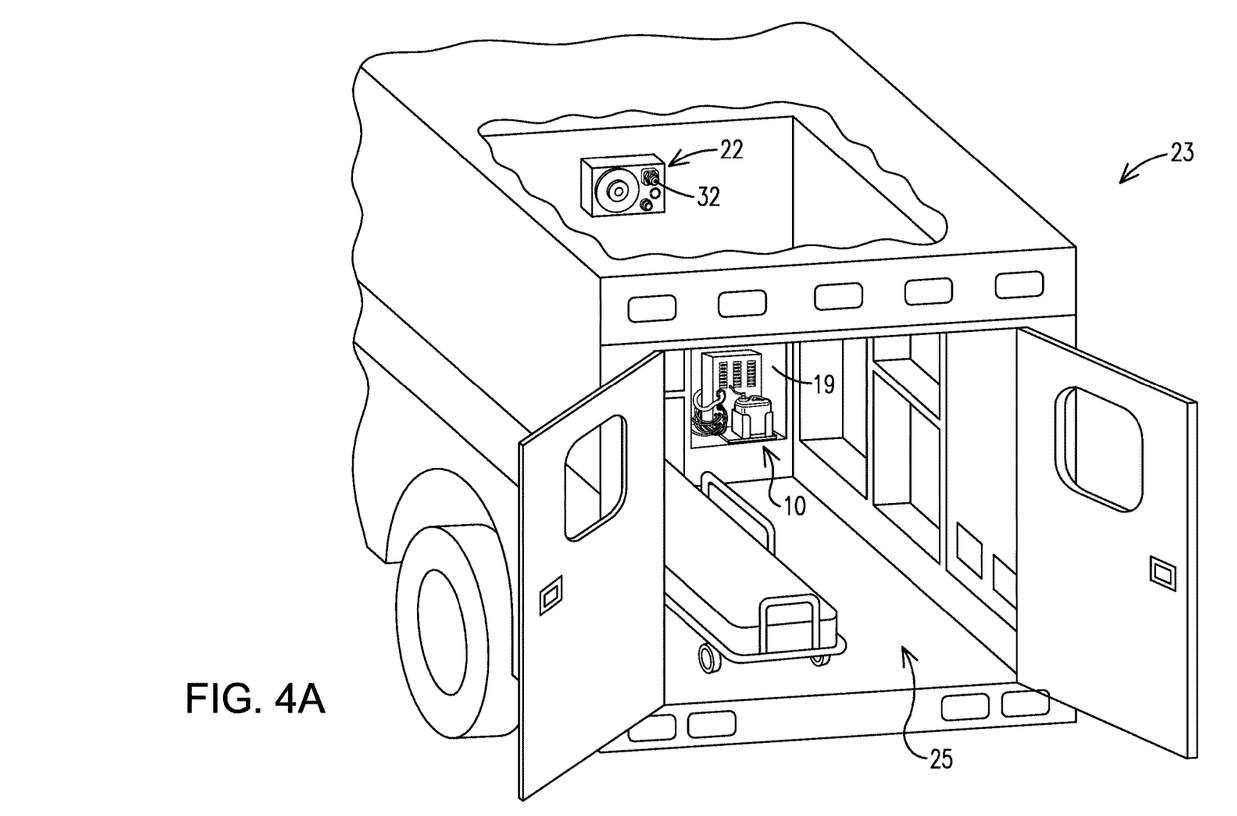
FIG. 4A is a rear perspective view of a vehicle with the decontamination system installed in a vehicle
Figure 4B:
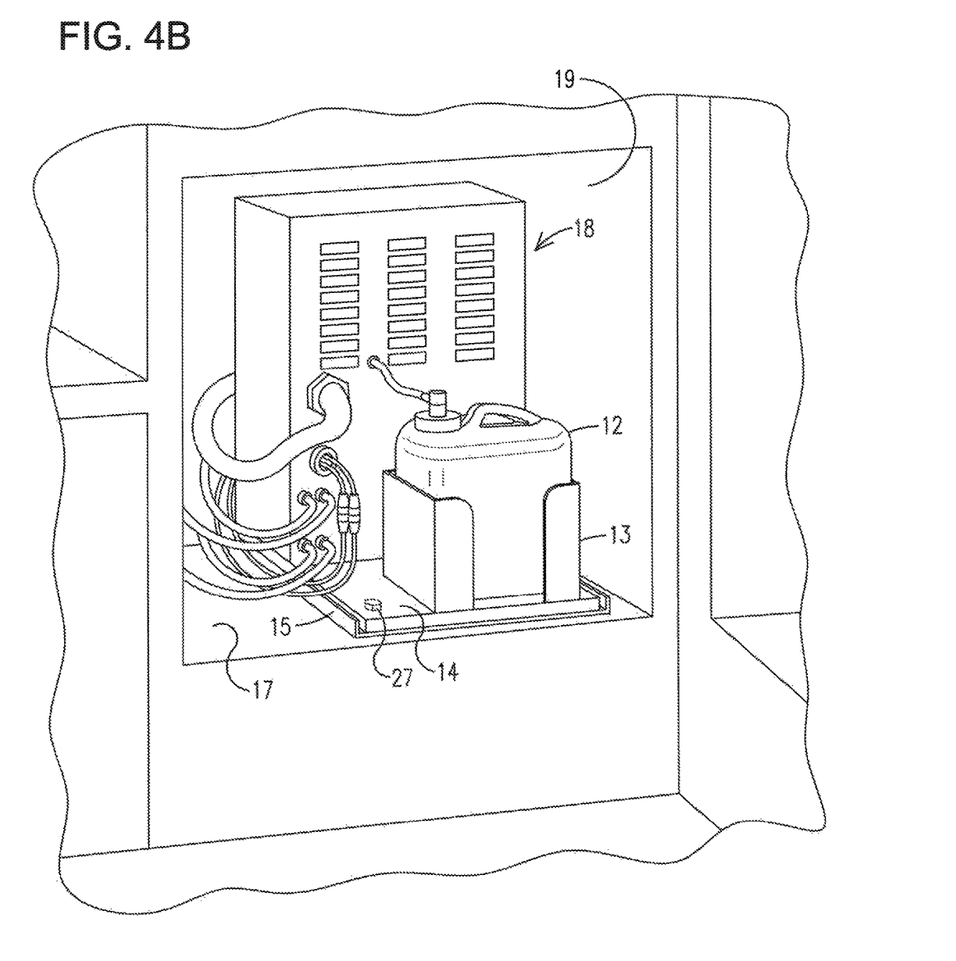
FIG. 4B is a perspective of the decontamination system of FIG. 4A.

In reference to FIGS. 4A and 4B, the support structure 18 is shown affixed to a surface 17 of a compartment 21 in an interior space of a vehicle 23, such as an interior passenger area of a motor vehicle (e.g. the patient area of an ambulance). The base plate 14 is positioned in sliding engagement on a planar track member 15. The track member 15 and base plate 14 are fixed to the compartment surface using known fastening mechanisms. By way of example, one or more bolts 27 extend through the base plate 14, track member 15 and compartment surface 17. When access to the support structure 18 and the reservoir 12 is necessary, the bolts 27 are removed and base plate 14 and the support structure 18 are slid along the track 15 for removal and access.

Figure 5:
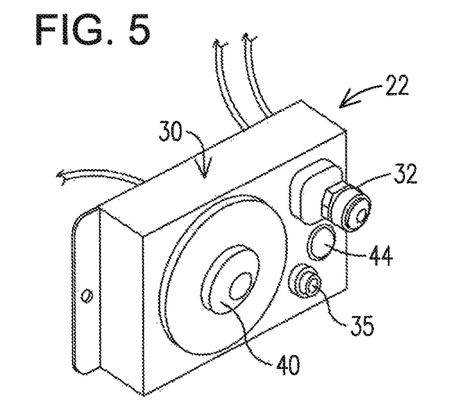
FIG. 5 is a perspective schematic view of a nozzle assembly of the decontamination system in accordance with aspects of the invention.
Figure 6:
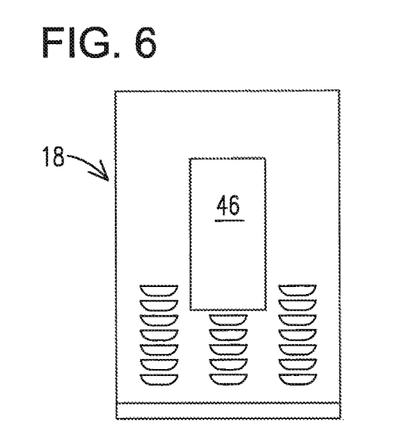
FIG. 6 is an end view of the decontamination system including a communications module.

A cover 18 of the housing has been removed in FIGS. 2 and 3, for purposes of illustrating components of the system 10. More specifically, the system 10 includes one or more sources of pressurized air such as one or more air compressors 20A, 20B that delivers pressurized air to a nozzle assembly 22 (FIG. 5). The source of pressurized air may be an air compressor integrated into system 10, or some vehicles have a compressed air source that can be accessed by system 10. For a two liter reservoir, a compressor 20 having a 0.8cfm at 30 psi may be used with system 10. An example of such a compressor is Model No. 910CDC22/ 12made by Gardner Denver Thomas Division located in Sheboygan, Wisconsin. In addition, one or more pumps 24, which are in fluid communication with the reservoir 12, deliver the disinfectant solution from the reservoir 12 to the nozzle assembly 22. Embodiments may include multiple pumps each pump being associated with a corresponding nozzle, in which case smaller pumps such as peristaltic pumps may be used. Alternatively, larger pumps may be used to service multiple nozzles. An example of a peristaltic pump that may be used with system 10 is a 30 ml/min. pump sold by Gardner Denver Thomas.

The system 10 further comprises a programmable controller 26 to control the activation and deactivation of the air compressors 20 and pumps 24 to deliver the disinfectant solution on demand. An example of a controller that may be used with system 10 is an Idec-Microsmart Pentra programmable logic control. Such a controller includes RAM and ROM modules or devices and may have SD card capabilities. In an embodiment, one or more relays 27 are provided in electrical communication with the controller 26 and the one or more compressors 20. In an embodiment, the system 10 may include two compressors and the relays 27 serve as the main power switches for the air compressors 20.

In addition, a sensor 28 is provided to detect levels of a disinfectant compound associated with the solution. In the example of a hydrogen peroxide disinfectant solution, the sensor 28 detects levels of hydrogen peroxide in an interior space of the vehicle. As will be explained in more detail below the sensor 28 is in signal communication with the controller 26, which may be programmed to send various commands or electrical signals in response to the level of disinfectant compound detected to control operations of the decontamination system 10.

The terms "in signal communication" or "in electrical communication" may be used interchangeably herein and are intended to mean the transmission of an electrical current, raw data, processed data, programmed instructions, programmed commands and the like so certain functions or operation of the system may be performed.

The system 10 may also include a standard DC-DC converter that for example may be linked to a 12 volt vehicle power source to provide 24 volt DC to components of the system 10.

While the decontamination system 10 is illustrated in connection with the above-described support structure 18, embodiments are not so limited. For example, each of the above-described components may be individually secured on interior walls or surfaces of the vehicle, or some of the components may be housed in a control box mounted within the vehicle. The term support structure is intended to mean any sort of structure that supports, holds, retains or contains one or more components of a decontamination system.

A nozzle assembly 22 is depicted in FIG. 5 and may be mounted to the vehicle in the interior space of the vehicle to be decontaminated. As shown, the nozzle assembly 22 includes various components that perform different functions associated with the operation of the decontamination system 10. While these components are shown configured as a single assembly, one skilled in the art will appreciate that each such component may be mounted in the vehicle as separate units performing the same functions.

Again with respect to FIG. 5, the assembly 22 comprises a nozzle 32 through which the disinfectant solution is delivered under pressure with compressed air to atomize the solution in order to generally, uniformly disperse the solution throughout the interior space to be decontaminated. As shown, the nozzle 32 is mounted to housing 30 in which fluid lines not shown) are housed and connected to the nozzle 32. Embodiments may include multiple nozzles in fluid communication with the reservoir 12. In addition, or alternatively, the nozzle 32 or nozzles may not be mounted on housing 30 and may be mounted to the support structure 18 or positioned elsewhere in the interior space to be decontaminated.

In a preferred embodiment in which an 0.2% wt aqueous chlorine dioxide solution, or an 8% vol. aqueous hydrogen peroxide solution, is used the amount of solution necessary to necessary to sanitize the vehicle 23 or interior space 25 is about 0.35 ml/ft$^3$. Accordingly, for in interior space, for example, having a volume of 12'×12'×8' or 1,152 ft$^3$ then a total of 403.2 ml is preferably dispersed in the interior space. If the controller 26 and pumps 24 are configured to deliver the solution at flow rate of 60 ml/minute for the system 10 that has two functioning nozzles 32 then the total amount of injection time would be 6.72 minutes. As will be explained in more detail below a dose amount or injection time may he input into the controller 26 to initiate a decontamination operation.

The system 10 may also include a flow meter 34 (FIG. 2) to monitor the flow rate of the solution from the reservoir 12 to the nozzle 32 or the amount of solution delivered to the nozzle(s) 32. The flow meter 34 is in signal communication with the controller 26 and transmits signals to the controller 26 indicative of the amount of solution having been delivered to the nozzle(s) 32. When an entered dose amount has been reached the controller 26 is programmed to deactivate the pumps 24 and compressor 20. In addition, controller 26 may be programmed to determine the amount of solution remaining in the reservoir based on signals received from the flow meter 34. A flowmeter that may be used with system 10 is a 101 Flosan sold by McMillan Company.

Again in reference to FIG. 5, the nozzle assembly 22 may further comprise an inlet portal 35 that is in fluid communication with the sensor 28 via a fluid line so that the sensor 28 may sample air in the interior space in which the disinfectant solution is dispersed and monitor the levels of a disinfectant compound (e.g., hydrogen peroxide) is present in the interior space during the course of a decontamination procedure. A vacuum pump 36, shown in FIG. 2, is in fluid communication with the inlet portal 35 and the sensor 28 via one or more fluid flow lines to draw air from the interior space through the inlet portal 35 and to the sensor 28. A sensor that may be used for detecting levels of hydrogen peroxide is a Draeger H$_2$O$_2$ LC with a Draeger Polytron 5000 sensor controller. Accordingly, the sensor 28 may include a chamber 37 and programmable controller or board 39, the operation of which is known to those skilled in the art.

The sensor 28 may be in signal communication with the controller 26 to send signals indicative of the detected level of sanitizing compound in the interior space. Data is provided relative to acceptable levels of the disinfectant compound present in the interior space for humans to enter, and this data is accessible by the controller 26. For example, signals received from the sensor 28 may be compared to this data to determine if a safe level of disinfectant compound in the interior space has been reached. Once these acceptable levels are reached the controller 26 may generate a signal indicating entry into the interior space is safe. The signal generated by the controller 26 may activate a visual or auditory safety signal, or it may result in deactivation of an auditory or visual warning signal. Alternatively, the sensor 28 may be configured to be programmable to access the above-referenced data associated with acceptable levels of the sanitizing compound and provide the above-described functions of the controller 26. A valve 38 in the fluid flow lines to the sensor 28 is disposed between the vacuum pump 36 and inlet portal 35, wherein during sampling of air from the interior space the valve 38 is in a first position. When the valve 38 is in a second position, air from outside the vehicle and/or interior space is delivered to flush or purge the sensor 28 to maintain or extend the life of the sensor 28.

As further shown in FIG. 5 the decontamination system 10 may include a motion detector 40. In this embodiment, the motion detector 40 is mounted as a component of the nozzle assembly 22; however, the motion detector 40 may be positioned at some other location of the interior space of the vehicle apart from the nozzle assembly 22 and/or components thereof. The motion detector 40 is configured for signal communication with the controller 26 to indicate whether or not a person is in the interior space before a decontamination operation is performed. The controller 26 may be programmed such that a decontamination operation is initiated only if no movement is detected for a preset time duration before the pumps 24 and air compressors 20 are activated to start delivery of the sanitizing solution and compressed air to the nozzle 32.

Figure 9:
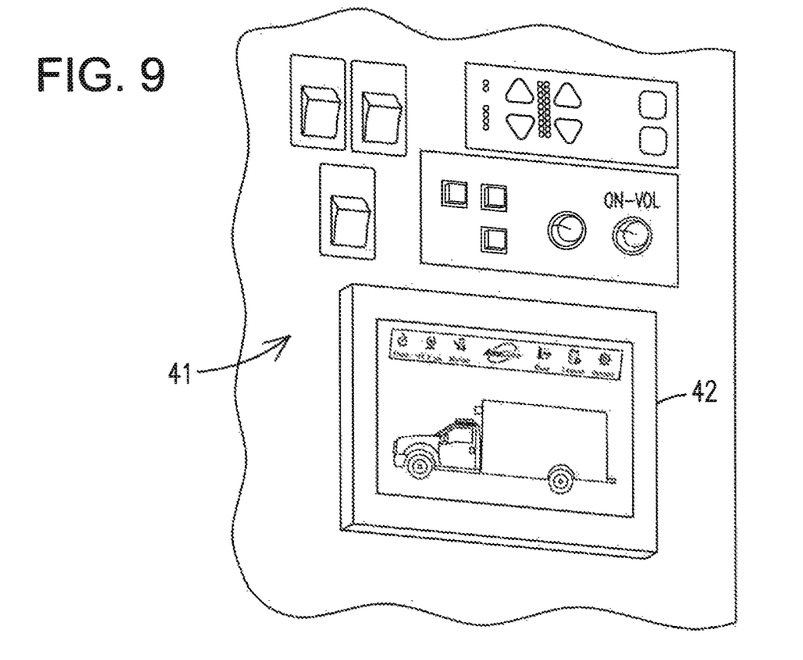
FIG. 9 is a perspective view of a touchscreen input device and display.

As shown, the system 10 comprises an input device 42, which may be a touchscreen display. The decontamination system 10 may be configured for an ambulance and the and the input device 42, such as a touchscreen may be located in the cab of the ambulance as depicted in FIG. 9; and, the interior space 25 (FIG. 4A) to be decontaminated may be the patient area behind the cab separated by a partition and a window.

Figure 8:
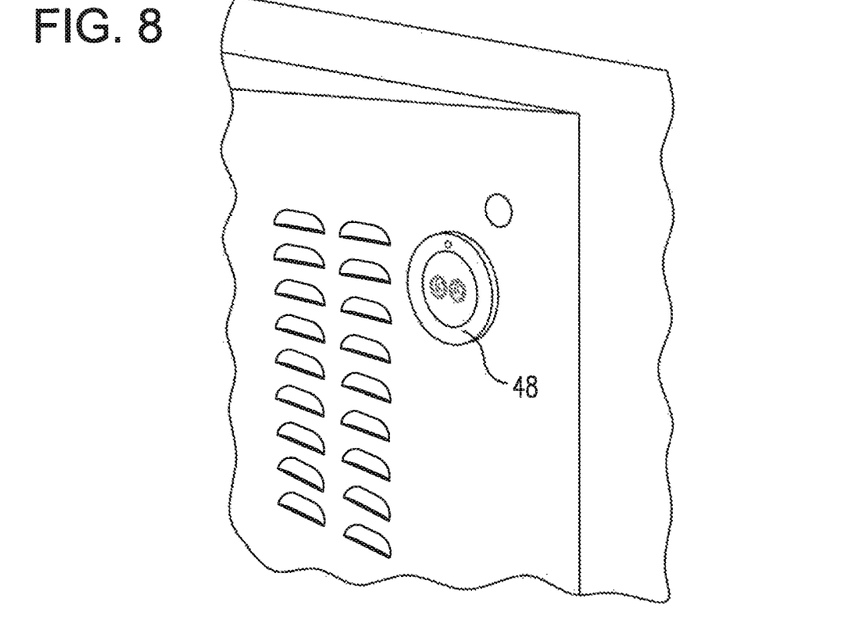
FIG. 8 is a perspective view of a hose connection port located in an external storage compartment of a vehicle.

Embodiments of the decontamination system 10, shown in FIG. 8 may include one or more external hose connection ports 48 that are mounted to an external part of the vehicle 23. The connection port 48 is mounted within an external compartment of a vehicle such as an ambulance. This port 48 is in fluid communication with the reservoir 12. In this manner, hoses with nozzle heads may be connected to the reservoir 12 for delivery of disinfectant solution and pressurized air nozzles, which may or may not be hand-held. Alternatively, nozzles may be permanently mounted at the port 48, or mounted for disengagement so the nozzles can be connected to the port then removed after a decontamination operation. In this manner, external surfaces of the vehicle may be treated with the disinfectant solution.

Figure 7:
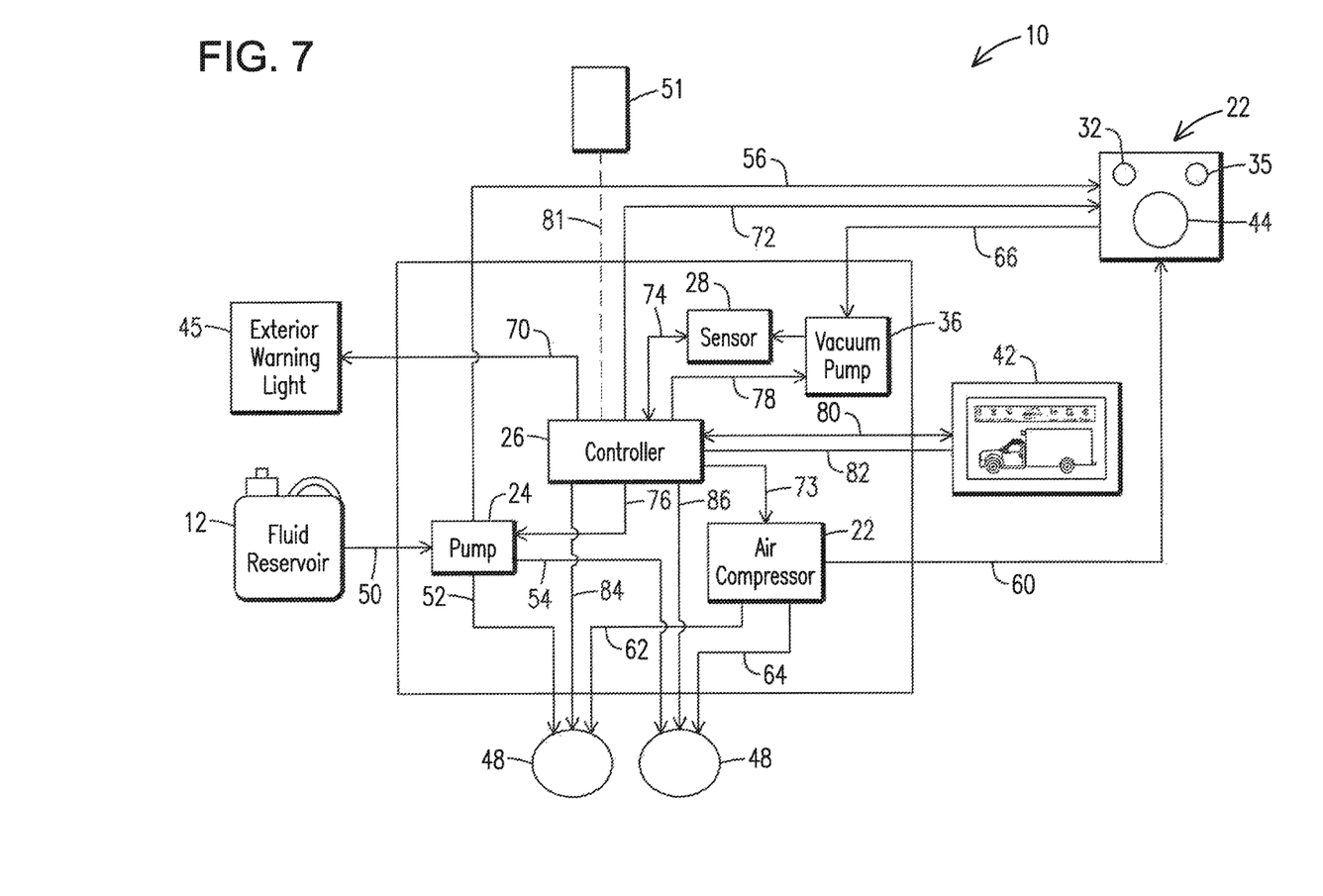
FIG. 7 is a schematic diagram of the decontamination system fluid flow, air flow direction, signal direction, electrical lines and Ethernet cables.

A schematic illustration of the electrical signal communication and fluid flow interconnection of components of the decontamination system are illustrated in FIG. 7. More specifically, FIG. 7 schematically shows the fluid flow lines and directions of fluid flow; and, the schematic shows the electrical or signal lines and direction of flow of information. With respect to FIG. 7, fluid flow lines 50, 52, 54, 56, which may be 0.25 inch flexible, plastic tubing, are illustrated providing fluid flow communication from the reservoir 12 to the nozzle 32 and external connection ports 48, and from the inlet portal 35 on the nozzle assembly 22 to the sensor 28. As shown, line 50 controls fluid flow from the reservoir 12 to the pump 24, lines 52 and 54 control fluid flow of the disinfectant solution from the pump 24 to the external outlets 48, and line 56 controls fluid flow of the disinfectant solution from the reservoir 12 to the nozzle assembly and nozzle 32.

In addition air flow lines 60, 62, and 64 provide fluid flow communication between the air compressor 20 nozzle 32 and external ports 48. In this manner, pressurized air is supplied to the nozzle 32 simultaneously with solution to atomize the solution as it is injected into are or onto a surface to be decontaminated. Also, fluid flow line 66 provides fluid flow communication between the inlet port 35 and the sensor 28 to detect and monitor the amount of disinfectant that is present in a vehicle.

With respect to FIG. 7, signal and/or electrical lines for the system 10 are schematically represented. Electrical lines 70, 72 provide electrical connection from a power source, preferably through the controller 26, to the exterior warning light 45 and the internal warning light 44, respectively. The controller 26 is in signal communication with the one or more pumps 24 via electrical line 76 to activate or deactivate the pumps 24 during the course of decontamination operations. Line 73 provides signal communication between the controller 26 and air compressor 22 to activate and deactivate the air compressor 22 for decontamination operations.

The controller 26 is also in electrical and/or signal communication with the sensor 28, via one or more lines 74, to power the sensor and for transmission of raw data relative to the level of disinfectant detected. In addition, line 80 is provided to activate or deactivate the vacuum pump 36 to collect air from the area being decontaminated. As will be described in more detail below, the controller 26 may be programmed to process the raw data to determine the level (or concentration) of the disinfectant or disinfectant compound is present in area during or after decontamination. Alternatively, the sensor 28 may include some level of a controller that is capable of processing that raw data to determine the level of a disinfectant in an area, such processed data may be transmitted to the controller 26 which controls certain system functions in response to the processed data.

While the system 10 is disclosed as including a sensor 28, the invention 10 is not so limited and may be operable without a sensor that detects and monitors levels of a disinfectant, or disinfectant compound in an interior area of a vehicle. For example, a sensor may not be required for milder disinfectants, such as the above-described aqueous chlorine dioxide solution or oxychlorine solution. To that end, the system does not require the motion detector 40, and may be operable without a motion detector.

As further shown a communications cable 78 such as an RJ-45 Ethernet cable provides connection between the input device 42, such as a such as a touchscreen display, and the controller 26 to enter parameter data associated with a disinfectant operation. As indicated above, this input device 42 (such as a touchscreen monitor or display), may be mounted somewhere in the cab of the vehicle such as the console area 41. The input device 42 may alternatively be a hand-held device such as a smart phone, hand-held computer lap-top or other computer device, that is linked with a local network and communication with the controller 26 may be conducted through the above-referenced communications module 46. Alternatively, an Ethernet cable 81 (for example, an RJ-45 Ethernet cable) may be provided to signal communication between the controller and input device 51, which may be a component of a local wireless network. Lines 82, 84, 86 are provided for electrical grounding of the system 10.

Figure 10:
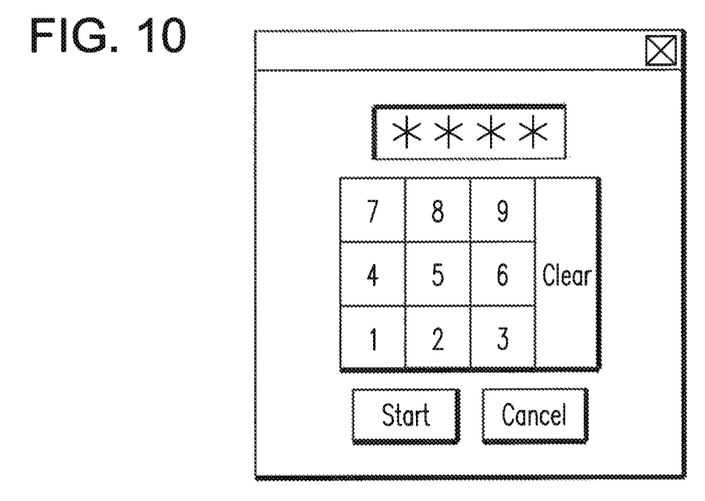
FIGS. 10-16 are drawings of a touchscreen display in accordance with a decontamination operation of the subject invention.
Figure 11:
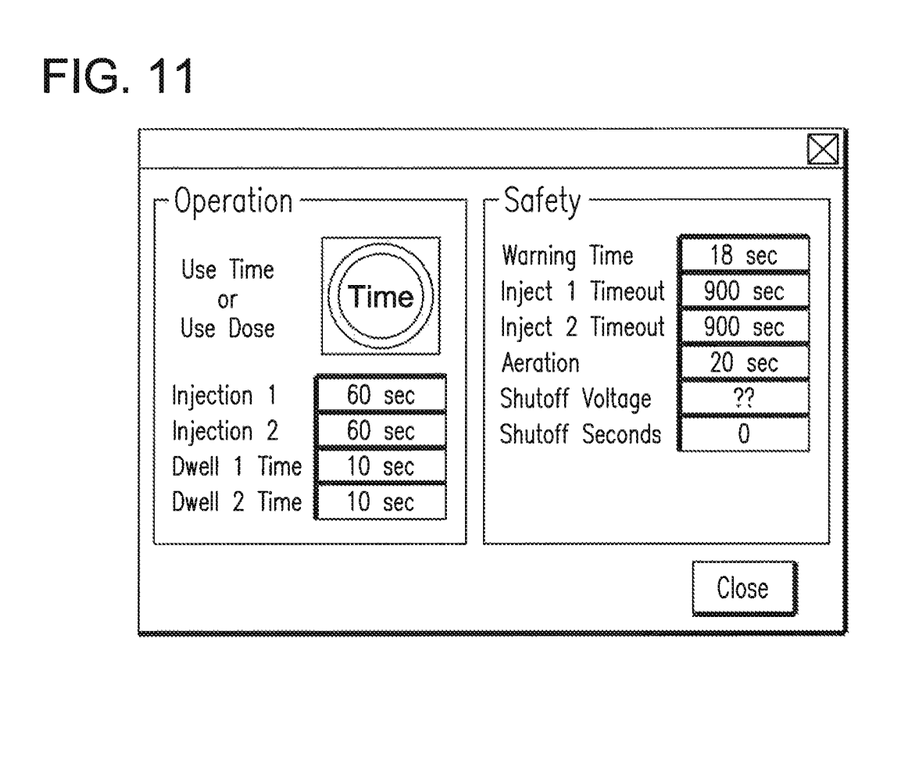
Figure 12:
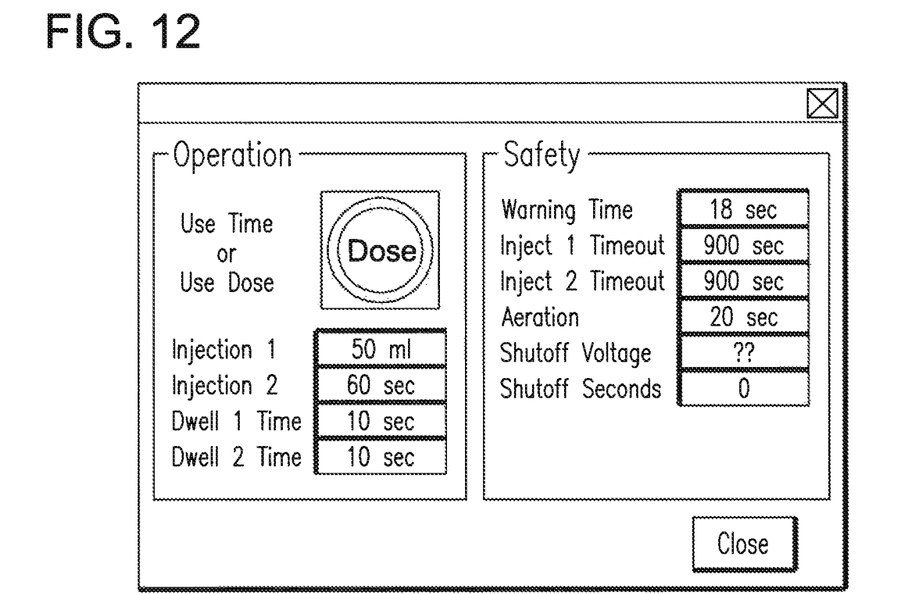
Figure 13:
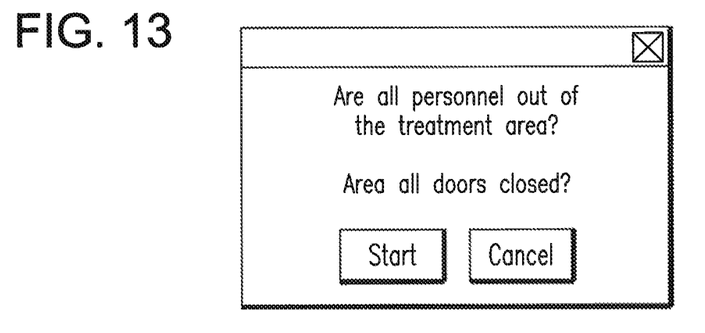

Images of sample screen displays that may be used for a decontamination operation are shown in FIGS. 10-16. In order to initiate a decontamination procedure, authorized personnel may login to the system 10, preferably using a passcode as seen in FIG. 10. The system 10 may further prompt the personnel to enter data relative to date, time, vehicle identification and location of the vehicle to initiate the decontamination procedure. In addition, the screen display may prompt the personnel to select a mode of operation, namely "Time" or "Dose." For a "Time" mode the total injection time is entered and in the "Dose" mode the total volume of disinfectant solution to be used is entered. As shown in FIG. 11 for "Time", the screen will display data related to the different phases of the decontamination operation, at which time the personnel may choose to change any of the listed variables. As further shown in FIG. 12, for the "Dose" mode the amount (volume) of disinfectant to be delivered for each injection 1 and 2 may be entered. After entry of decontamination procedure data, a "START" button or icon (FIG. 13) will appear and authorized personnel presses the button or icon.

Figure 14:
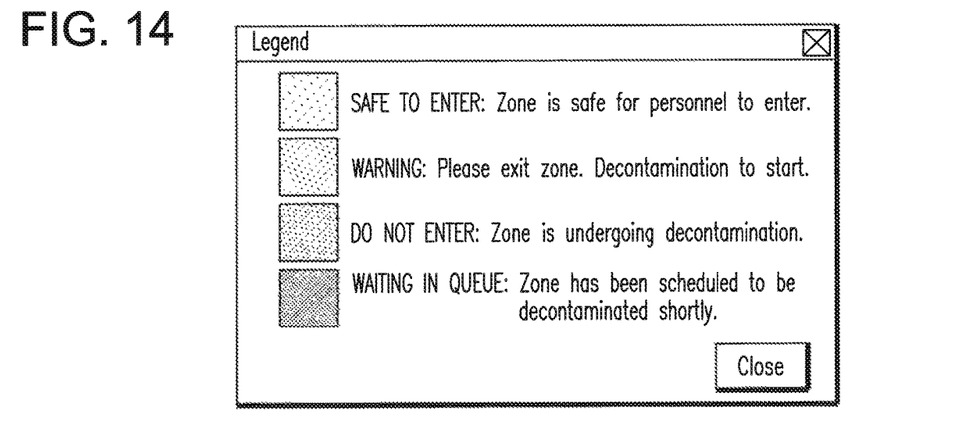
Figure 15:
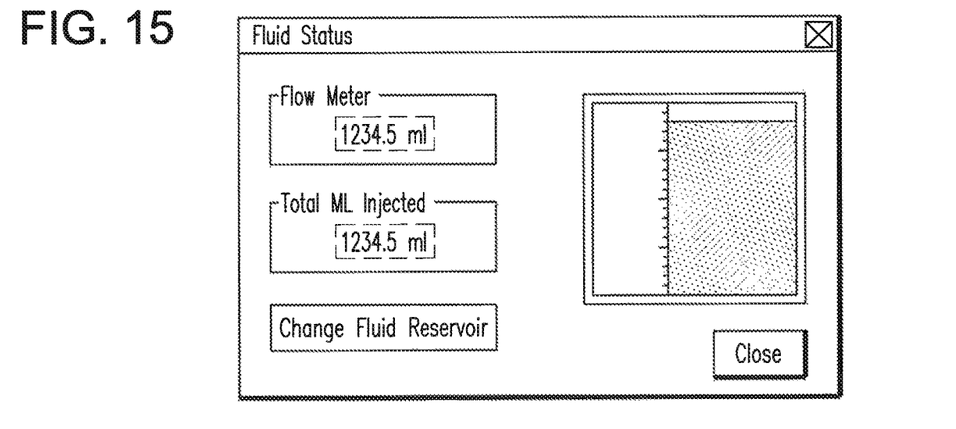
Figure 16:
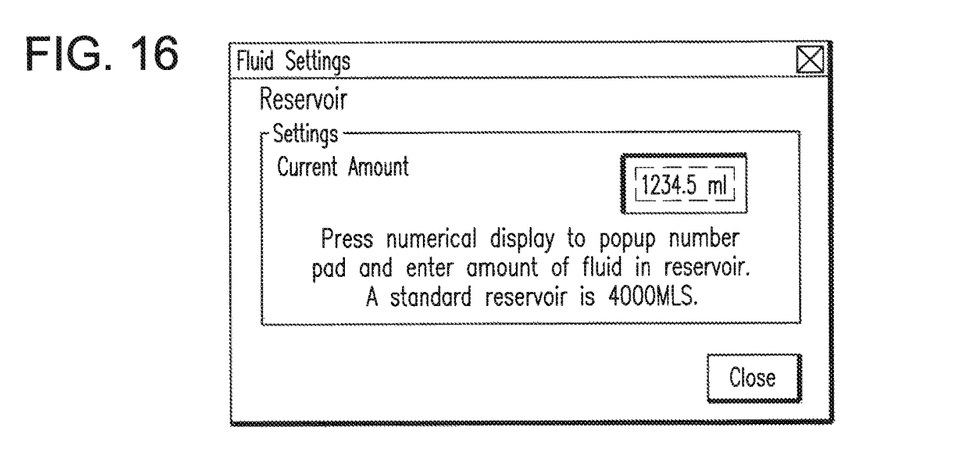

Once started, a visual or auditory warning signal is started for personnel to exit the interior space. As shown in FIG. 14, this warning signal may include a yellow light or indicator. In embodiments, the controller 26 is configured with a time delay wherein after a preset time duration during which the motion detector 40 detects no motion, i.e., no personnel in the interior space to be decontaminated, the controller 26 initiates certain vehicle operations. More specifically, the controller 26 is linked to the vehicle's internal communication (the vehicle CAN bus) or computer system to determine if certain vehicle functions are performed. For example, the controller may transmit one or more control signals to turn the ignition off, lock the doors of the interior space, turn off HVAC functions, close windows, etc. To that end, the vehicle communication system may transmit signals to the controller 26 indicative of the status of these vehicle operations. These functions may be performed during a first time period that may be referred to as a staging mode; and, a warning light or strobe and/or an audible signal may be activated such as the light 44 on the nozzle assembly 22. In addition, an exterior light 45 (FIG. 7) on the vehicle may be electrically linked to the controller 26 and activated. However, if motion is detected during this staging mode or first time duration, the controller 26 will not initiate the operations associated with the staging phase.

Once the first time duration (staging phase) has elapsed and the vehicle operations described above are completed, the controller 26 activates the pumps 24 and air compressors 20 to deliver the disinfectant solution and compressed air to the nozzle 32 to atomize the solution and inject the same into the interior space. The time duration of this injection mode may vary according to the volume of the interior space and the volume of disinfectant solution need to decontaminate the space. To that end, as provided in FIG. 11, the injection mode may be divided into discrete timed periods including one or more dwell times during which no disinfectant solution is injected interposed between two injection periods. By way of example, an injection may be made continuously for 4 minutes for a first injection period followed by a 2 minute first dwell time, which is then followed by a second 4 minute injection period followed by a second 2 minute dwell time for an injection phase lasting 12 minutes. During the injection, and as represented in FIG. 14, a red warning signal may be displayed indicating the vehicle is undergoing decontamination.

After the injection mode has been completed, an aeration mode is initiated by the controller 26 transmitting one or more signals to activate the vehicle HVAC system/supplemental exhaust blower. Note, in an embodiment the warning lights and audible signals may remain on during the staging, injection and aeration modes. During the aeration mode, the sensor 28 detects levels of sanitizing compound within the interior space. The controller 26 may be programmed such that once the level of the detected disinfectant compound has dropped to a predetermined threshold for a pre-determined time duration, signals are generated to turn off the HVAC/supplemental exhaust blower and unlock doors to the vehicle. For example, if hydrogen peroxide is the detected compound the threshold concentration may be 1 ppm and the time duration may be 3 minutes. In addition, the warning signals may be deactivated or changed to indicate that it is safe for authorized personnel to enter the interior space and decontamination has been completed. As shown in FIG. 14, a green light may indicate the interior space and vehicle is safe for personnel to enter.

As further shown in FIG. 14, the controller 26 and touchscreen display may be configured to display, when a decontamination operation is completed, an amount of disinfectant solution used and an amount of disinfectant solution remaining in the reservoir 12. With respect to FIG. 15, to the extent that disinfectant solution is added to the reservoir 12, the amount of disinfectant solution in the reservoir 12 may be updated by inputting the data at the touchscreen.

With respect to FIG. 5, the system 10 may comprise a communications module 46 that may be linked to a local wireless network for transmission data relative to the decontamination procedure vehicle generated by the decontamination system to a local server or wireless network 47 (FIG. 7). Such data may include the vehicle identification, date of decontamination, the time decontamination was initiated and ended, the amount of disinfectant solution used during the decontamination procedure and the personnel involved in implementing the decontamination procedure. This may be particularly useful for entities such as a hospital, police department, transit system, airline, etc., that maintain a fleet of vehicles and desire to monitor decontamination of each vehicle in a fleet of vehicles.

While certain embodiments of the present invention have been shown and described herein, such embodiments are provided by way of example only. Numerous variations, changes and substitutions will occur to those of skill in the art without departing from the invention herein. Accordingly, it is intended that the invention be limited only by the spirit and scope of the appended claims.

What is claimed is:

1. A decontamination system on-board a vehicle, comprising:
   a reservoir secured on-board a vehicle and containing a disinfectant solution;
   a pressurized air supply secured on-board the vehicle;
   one or more nozzles secured on-board the vehicle and in fluid communication with the reservoir and the pressurized air supply, wherein at least one nozzle is mounted within an interior space of the vehicle;
   one or more pumps secured on-board the vehicle and the one or more pumps are in fluid communication with the reservoir and the one or more nozzles; and
   a programmable controller in signal communication with the one or more pumps and pressurized air supply to activate the one or more pumps and pressurized air supply to deliver the disinfectant solution and pressurized air to the one or more nozzles, wherein the solution is dispersed in atomized form in the interior space of the vehicle to be decontaminated.

2. The decontamination system of claim 1 wherein the controller is in signal communication with a vehicle electrical or communication system to initiate and monitor vehicle operations in preparation for a decontamination operation and before disinfectant solution is delivered to the one or more nozzles.

3. The decontamination system of claim 1 further comprising a disinfectant sensor secured on board the vehicle and in fluid flow communication with the interior space and that detects levels of an active disinfectant compound of the atomized disinfectant solution.

4. The decontamination system of claim 3 further comprising a nozzle assembly including the nozzle, a motion detector and an inlet port all mounted on a same bracket in the interior of the vehicle to be decontaminated, and the inlet port is in fluid flow communication with the disinfectant sensor.

5. The decontamination system of claim 1, further comprising a motion detector on-board the vehicle and for detecting presence of personnel in the interior space, and the motion detector is in signal communication with the controller.

6. The decontamination system claim 5, wherein the controller is programmed such that when a decontamination operation is initiated the controller activates the one or more pumps and pressurized air supply after a predetermined time during which the motion detector does not detect movement within the interior space.

7. The decontamination system of claim 1, further comprising one or more connection ports mounted to an exterior of the vehicle and in fluid communication with the reservoir and pressurized air supply and the ports are configured for connection to nozzles to sanitize an exterior of the vehicle.

8. The decontamination system of claim 1 wherein the nozzle is mounted to an interior surface defining the interior space of the vehicle.

9. The decontamination system of claim 1 wherein the vehicle is a motor vehicle and wherein the interior space comprises an interior passenger area of the motor vehicle.

10. A decontamination system on-board a vehicle, comprising:
    a support structure mounted to a surface within an interior space of the vehicle to be decontaminated;

a reservoir secured on the support structure and containing a disinfectant solution;

a pressurized air supply secured on-board the vehicle;

one or more nozzles secured on-board the vehicle and in fluid communication with the reservoir and the pressurized air supply wherein at least one nozzle is mounted within the interior space of the vehicle;

one or more pumps secured on the support structures and the one or more pumps are in fluid communication with the reservoir and the one or more nozzles; and a programmable controller in signal communication with the one or more pumps and pressurized air supply to activate the one or more pumps and pressurized air supply to deliver the disinfectant solution and pressurized air to the one or more nozzles, wherein the solution is dispersed in atomized form in the interior space of the vehicle to be decontaminated.

11. The decontamination system of claim 10, wherein the support structure includes a base plate and one or more upright frame members mounted to the base plate, and the one or more pumps are mounted to the one or more upright frame member.

12. The decontamination system of claim 11, wherein the support structure includes a plurality of upright retainer walls configured to secure the reservoir on the support structure.

13. The decontamination system of claim 12, wherein the base plate is mounted in sliding engagement with a track that is fixed to the surface within the interior space of the vehicle to be decontaminated.

14. The decontamination system of claim 11, further comprising a disinfectant sensor mounted to the one or more upright frame members and in fluid flow communication with the interior space and that detects levels of an active disinfectant of the atomized disinfectant solution.

15. The decontamination system of claim 10, wherein the support structure includes a base plate and one or more upright frame members mounted to the base plate and the controller is mounted to the one or more upright frame member.

16. The decontamination system of claim 15, wherein the one or more pumps are mounted to the one or more upright members.

17. The decontamination system of claim 16, further comprising a housing cover disposed over the upright members.

18. The decontamination system of claim 10, wherein the controller is in signal communication with a vehicle communication system to initiate vehicle operations in preparation for a decontamination operation and before disinfectant solution is delivered to the one or more nozzles.

19. The decontamination system of claim 10, further comprising a motion detector on-board the vehicle and for detecting presence of personnel in the interior space, and the motion detector is in signal communication with the controller.

20. The decontamination system of claim 10 wherein the disinfectant solution comprises at least one of a hydrogen peroxide and chlorine based compound.

* * * * *